United States Patent
Voegele et al.

(10) Patent No.: US 7,637,896 B2
(45) Date of Patent: Dec. 29, 2009

(54) OBTURATOR TIP ASSEMBLY FOR A TROCAR

(75) Inventors: Aaron C. Voegele, Loveland, OH (US); Mark S. Zeiner, Mason, OH (US); Paul T. Franer, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 431 days.

(21) Appl. No.: 11/092,743

(22) Filed: Mar. 30, 2005

(65) Prior Publication Data

US 2006/0229654 A1    Oct. 12, 2006

(51) Int. Cl.
*A61M 5/00* (2006.01)
*A61M 25/00* (2006.01)
(52) U.S. Cl. .................................... 604/264
(58) Field of Classification Search ............... 600/184, 600/204–210, 108, 219; 604/264; 403/9, 403/13–14, 263, 361, 329, 373; 285/307, 285/319, 913, 914
See application file for complete search history.

(56) References Cited

U.S. PATENT DOCUMENTS

| | | | |
|---|---|---|---|
| 5,375,938 A * | 12/1994 | Bartlow | 403/202 |
| 5,609,604 A | 3/1997 | Schwemberger et al. | |
| 5,618,297 A | 4/1997 | Hart et al. | |
| 5,709,671 A * | 1/1998 | Stephens et al. | 604/264 |
| 5,817,061 A * | 10/1998 | Goodwin et al. | 604/164.03 |
| 6,544,277 B1 * | 4/2003 | O'Heeron et al. | 606/185 |
| 2002/0026207 A1 * | 2/2002 | Stellon et al. | 606/185 |
| 2003/0075923 A1 * | 4/2003 | Lepoutre | 285/330 |
| 2005/0006433 A1 * | 1/2005 | Milliman et al. | 227/176.1 |

OTHER PUBLICATIONS

International Standard, Ref. No. ISO 594/1-1986, Conical Fittings with a 6% (Luer) taper for syringes, needles and certain medical equipment—Part 1: General Requirements, Jun. 15, 1986, Global engineering Documents, p. 2.*

* cited by examiner

*Primary Examiner*—(Jackie) Tan-Uyen T. Ho
*Assistant Examiner*—Dianne Dornbusch
(74) *Attorney, Agent, or Firm*—Welsh & Flaxman LLC

(57) ABSTRACT

A trocar obturator includes a shaft having a proximal end and a distal end. The shaft also includes an outer surface. A tip member is secured to the distal end of the shaft, the tip member including a first end and a second end, as well as an outer surface. A keyed coupling structure links the tip member to the shaft, wherein the shaft adjacent the tip member tapers to a surface diameter substantially coextensive with the outer surface of the tip member and the tip member adjacent the shaft tapers to a surface diameter substantially coextensive with the outer surface of the shaft.

18 Claims, 4 Drawing Sheets

OBTURATOR TIP ASSEMBLY FOR A TROCAR

BACKGROUND OF THE INVENTION

1. Field of the Invention

The invention relates to trocars. More particularly, the invention relates to an obturator tip assembly for a trocar.

2. Description of the Prior Art

A trocar assembly is a surgical instrument used to gain access to a body cavity. A trocar assembly generally comprises two major components, a trocar sleeve, composed of a trocar housing and a trocar cannula, and a trocar obturator. The trocar cannula, having the trocar obturator inserted therethrough, is directed through the skin to access a body cavity. Once the body cavity is accessed, laparoscopic or arthroscopic surgery and endoscopic procedures may be performed.

In order to penetrate the skin, the distal end of the trocar cannula is placed against the skin that has been previously cut with a scalpel. The trocar obturator is then used to penetrate the skin and access the body cavity. By applying pressure against the proximal end of the trocar obturator, the sharp point of the trocar obturator is forced through the skin until it enters the body cavity. The trocar cannula is inserted through the perforation made by the trocar obturator and the trocar obturator is withdrawn, leaving the trocar cannula as an access way to the body cavity.

The proximal end portion of the trocar cannula is typically joined to a trocar housing that defines a chamber having an open distal end portion in communication with the interior lumen defined by the trocar cannula. A trocar obturator, or other elongated surgical instruments or tools, axially extends into and is withdrawn from the trocar cannula through the proximal end portion of the chamber defined by the trocar housing.

Current trocar obturators have distal ends designed for passage through the various seal assemblies employed in trocars. The distal ends, or tips, of current trocar obturators are prone to disturbing the seal assemblies and consequently complicating the insertion and extraction process. In addition, prior art tip construction are generally difficult to manufacture and assemble. As such, a need exists for an improved trocar obturator tip construction obviating the shortcomings of the prior art trocar obturators. The present invention provides a trocar obturator tip construction obviating the shortcomings by providing structure permitting ready assembly of the tip and passage through the seal assemblies employed in trocar sleeves.

SUMMARY OF THE INVENTION

It is, therefore, an object of the present invention to provide a trocar obturator having a shaft with a proximal end, a distal end, and an outer surface. The trocar obturator further includes a tip member secured to the distal end of the shaft. The tip member includes a first end and a second end, as well as an outer surface. A coupling structure links the tip member to the shaft, wherein the shaft adjacent the tip member tapers to a surface diameter substantially coextensive with the outer surface of the tip member and the tip member adjacent the shaft tapers to a surface diameter substantially coextensive with the outer surface of the shaft.

It is also an object of the present invention to provide a trocar obturator wherein at least a portion of the shaft adjacent the tip member includes at least one abutment member and the first end of the tip member is shaped and dimensioned to receive the abutment member upon assembly of the tip member upon the distal end of the shaft. The abutment member is also substantially coextensive with the adjacent portions of the tip member.

It is also another object of the present invention to provide a trocar obturator wherein the distal end of the shaft includes a plurality of abutment members defining raised and lowered sections about the circumference of the shaft. The abutment members are substantially coextensive with the adjacent portions of the tip member.

It is a further object of the present invention to provide a trocar obturator wherein the first end of the tip member includes extension arms shaped and dimensioned for positioning with the respective lowered sections defined by the abutment members along the distal end of the shaft. The extension members are substantially coextensive with the adjacent portions of the shaft.

It is another object of the present invention to provide a trocar obturator wherein the shaft includes a coupling member along the distal end thereof for engagement with the tip member.

It is yet another object of the present invention to provide a trocar obturator wherein the coupling member is a snap coupling member biased to seat within a recess formed along an inner surface of the tip member.

It is also an object of the present invention to provide a trocar obturator wherein the shaft includes a plurality of snap coupling members biased to seat within respective recesses formed along the inner surface of the tip member.

It is still a further object of the present invention to provide a trocar obturator wherein the tip member includes an inner surface in which the distal end of the shaft is mounted during assembly, and the inner surface includes an inwardly directed lip limiting movement of the tip member relative to the shaft.

It is another object of the present invention to provide a trocar obturator wherein the distal end of the shaft includes at least one abutment member and the first end of the tip member is shaped and dimensioned to receive the abutment member upon assembly of the tip member upon the distal end of the shaft.

It is also another object of the present invention to provide a trocar obturator wherein the tip member includes an inner surface in which the distal end of the shaft is mounted during assembly, and the inner surface includes an inwardly directed lip limiting movement of the tip member relative to the shaft.

It is still another object of the present invention to provide a trocar obturator wherein the coupling structure is a keyed coupling structure.

Other objects and advantages of the present invention will become apparent from the following detailed description when viewed in conjunction with the accompanying drawings, which set forth certain embodiments of the invention.

DESCRIPTION OF THE PREFERRED EMBODIMENT

Figure 1:
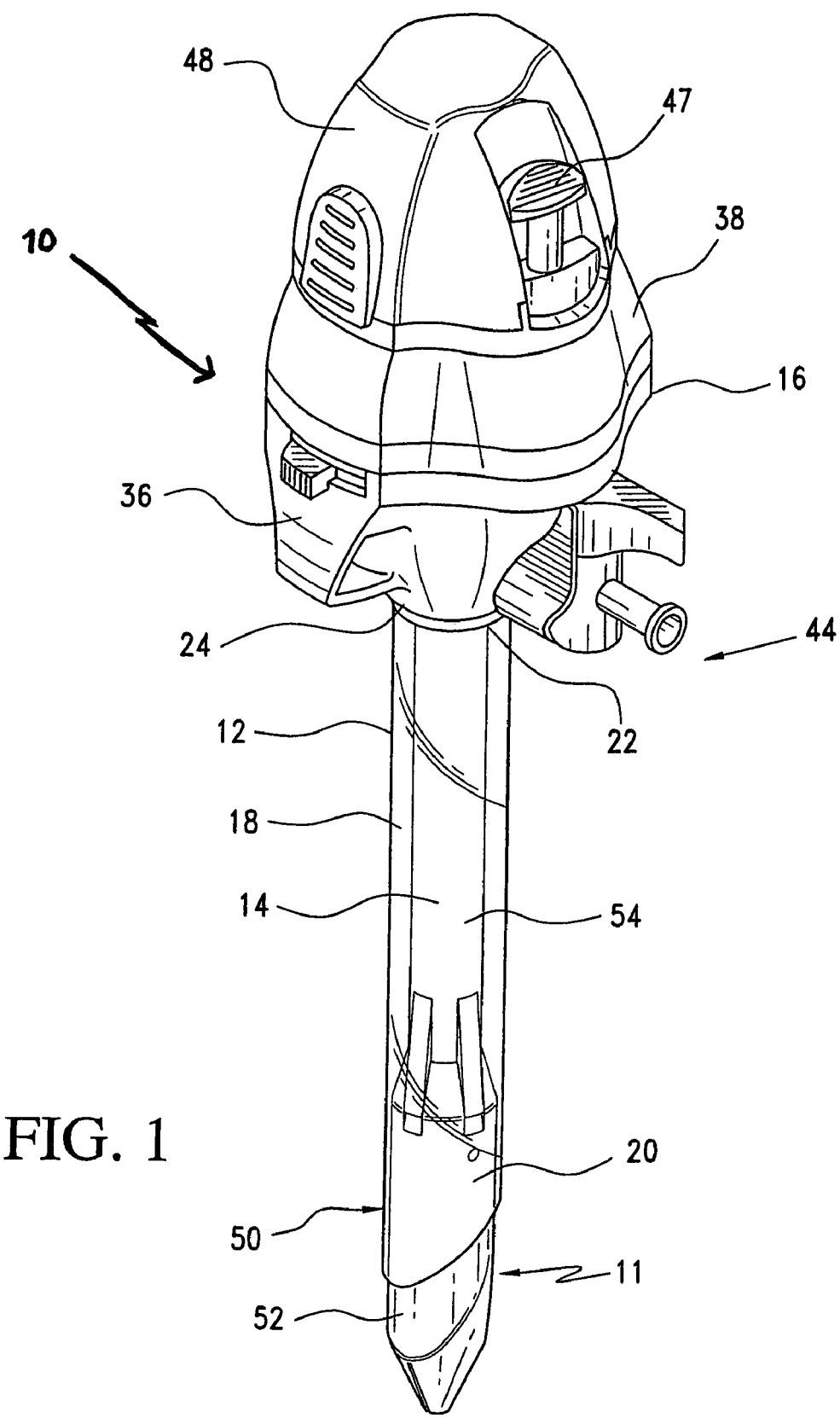
FIG. 1 is a perspective view of a trocar assembly in accordance with the present invention.
Figure 2:
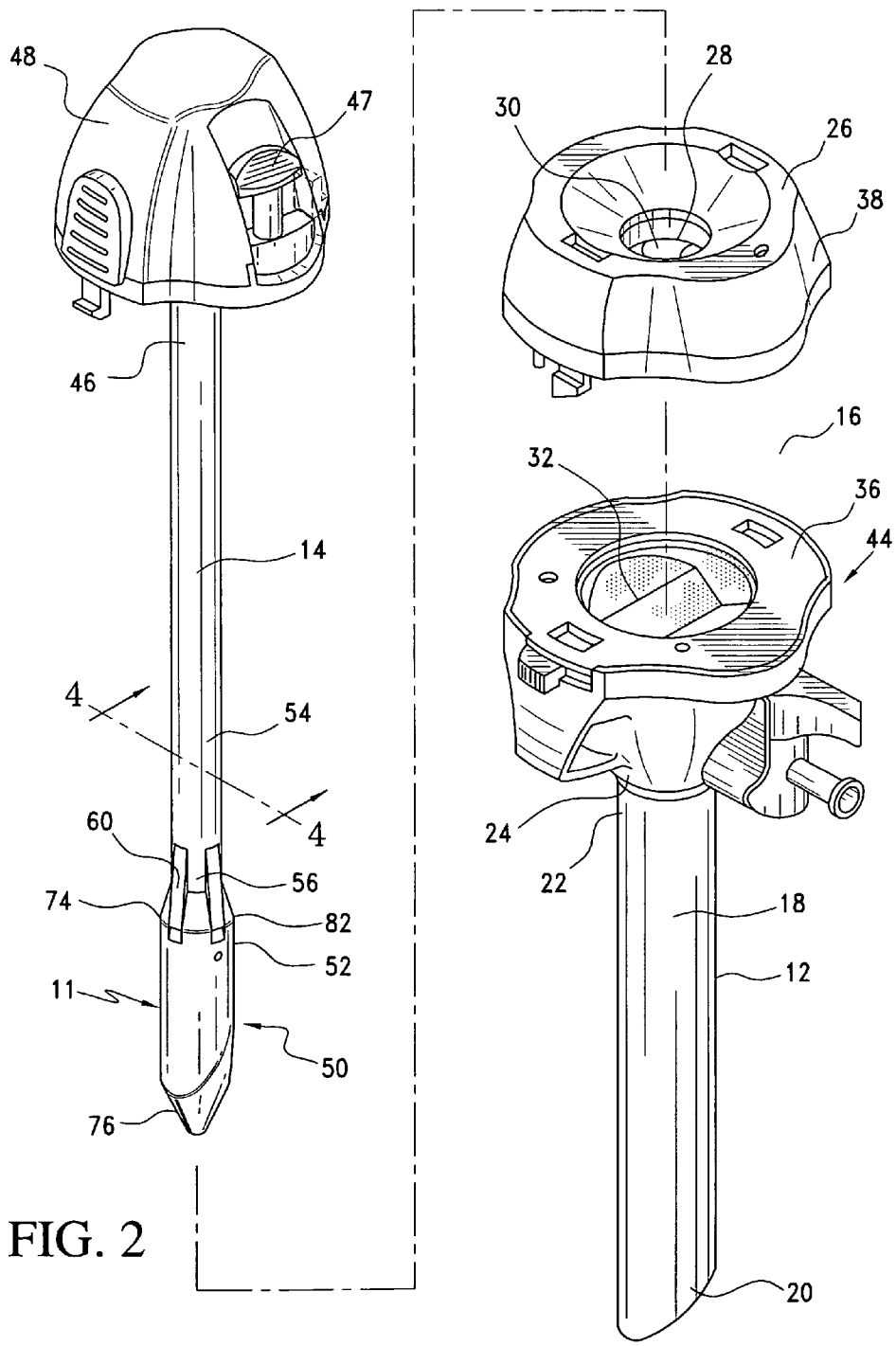
FIG. 2 is an exploded view of the trocar assembly shown in FIG. 1.

The detailed embodiment of the present invention is disclosed herein. It should be understood, however, that the disclosed embodiment is merely exemplary of the invention, which may be embodied in various forms. Therefore, the details disclosed herein are not to be interpreted as limited, but merely as the basis for the claims and as a basis for teaching one skilled in the art how to make and/or use the invention.

A tip structure 11 for a trocar obturator 14 is disclosed. The tip structure 11 provides for improved operation of the trocar obturator 14 as it is passed through the trocar cannula 12 and trocar housing 16. As those skilled in the art will certainly appreciate, the concepts underlying the present invention may be applied to a variety of trocar obturator structures without departing from the spirit of the present invention.

Referring to FIGS. 1 to 5, the trocar assembly 10 generally includes a trocar cannula 12, a trocar obturator 14, and a trocar housing (or handle) 16. For example, the present trocar obturator is designed for use with a trocar assembly such as that disclosed in U.S. patent application Ser. No. 10/943,215, filed Sep. 17, 2004, now published as U.S. Patent Application Publication No. 2005/0077688, entitled "MULTI-ANGLED DUCKBILL SEAL ASSEMBLY", published Apr. 14, 2005, which is incorporated herein by reference. However, those skilled in the art will appreciate the present trocar obturator may be used with a variety of trocar assemblies without departing from the spirit of the present invention.

Briefly, the trocar cannula 12 defines an interior lumen 18 having an open distal end portion 20 and an open proximal end portion 22. The proximal end portion 22 extends into and is mounted in the distal end portion 24 of trocar housing 16. The trocar housing 16 has an open proximal end portion 26 that defines an opening 28. The opening 28 is provided with a proximal seal assembly 30 constructed in accordance with the present invention and described in detail hereinbelow. The opening 28 is further provided with a duckbill seal assembly 32 positioned beneath the proximal seal assembly 28. While the present seal assembly is disclosed as a proximal seal assembly forming part of a dual sealing system, the present seal assembly may be utilized in a single seal system without departing from the spirit of the present invention.

In general, the trocar sleeve 44 is composed of a trocar cannula 12 and a trocar housing 16. The trocar housing 16 includes a first housing member 36 and a second housing member 38. Although, the housing 16 is disclosed as two components in accordance with a preferred embodiment of the present invention, it is contemplated that a single component could be used without departing from the spirit of the present invention. The two-component housing in accordance with a preferred embodiment of the present invention, aids in removal of specimens.

The trocar obturator 14 is slidable in and removable from within the trocar cannula 12 and is inserted into the trocar housing 16 and the trocar cannula 12 through the proximal seal assembly 30, the duckbill seal assembly 32 and the opening 28 of the trocar housing 16. An obturator handle 48 is provided at the proximal end 46 of the trocar obturator 14 and a blade (not shown), which is actuated via a lever 47 in a conventional manner, is formed at the distal end 50 thereof. As is well known in the art, the proximal seal assembly 30 cooperates with the exterior of the instruments (for example, trocar obturators and other tools adapted for use in conjunction with trocar based procedures) extending through the trocar sleeve 44 to sealingly engage the exterior surface thereof and thereby preclude the passage of fluids through the trocar housing 16.

Referring to FIGS. 1 to 8, the trocar obturator 14 in accordance with a preferred embodiment of the present invention will now be described in greater detail. The trocar obturator 14 generally includes a proximal end 46 to which a handle 48 is secured. The trocar obturator 14 further includes a distal end 50 including a tip member 52 forming the focus of the present disclosure. Between the distal end 50 and the proximal end 46 of the trocar obturator 14 is a shaft 54 that connects the tip member 52 to the handle 48.

In accordance with a preferred embodiment, the trocar obturator 14 is a polycarbonate. More particularly, the trocar obturator 14 is predominantly polycarbonate with additives added to particular components for additional lubrication. Ultimately, the materials used in accordance with, the present invention are conventional and those skilled in the art will appreciate that various materials may be used without departing from the spirit of the present invention.

With particular reference to the distal end 50 of the trocar obturator 14, the tip member 52 is secured to the shaft 54 along a joint providing a long interface between the tip member 52 and the shaft 54. The longer interface provides more strength to prevent bending and excessive deflection due to side loading. In addition, by providing a tip member 52 which is distinctly formed relative to the shaft 54, the tip member 52 may be formed in a different color than the shaft 54, providing for enhanced visualization of the tip member 52 of the trocar obturator 14. In addition, the present coupling structure allows for a larger diameter shaft to be used, which ultimately results in a stronger obturator than found in current prior art obturator designs made from plastics.

The tip member 52 is snapped onto the shaft 54. As will be appreciated based upon the following disclosure, the snap connection between the shaft 54 and the tip member 52 eases assembly and ultimately results in a stronger connection than found in prior art tip constructions. The snap connection, in conjunction with the increased overlap length between the shaft 54 and the tip member 52, results in the creation of a stronger joint between the tip member 52 and the shaft 54.

By providing a tip member 52 in accordance with the present invention, there is less need for coring of the trocar obturator and tooling shutoffs to achieve coring are eliminated. As those skilled in the art will certainly appreciate, coring refers to a step in the injection molding process. The present tip member 52 is separate from the shaft 54 during molding. By making both the shaft 54 and the tip member 52 as two separate components, each are easier to produce. Coring has previously been difficult to achieve and is rather expensive as the additional shutoffs in the tooling increase mold complexity and maintenance. The present invention simplifies the coring procedure and saves substantial money. In addition, by providing a tip member in accordance with the present invention, the same shaft maybe utilized for both 11 mm and 12 mm designs by simply securing a different tip member to the same shaft.

Figures 3, 4:
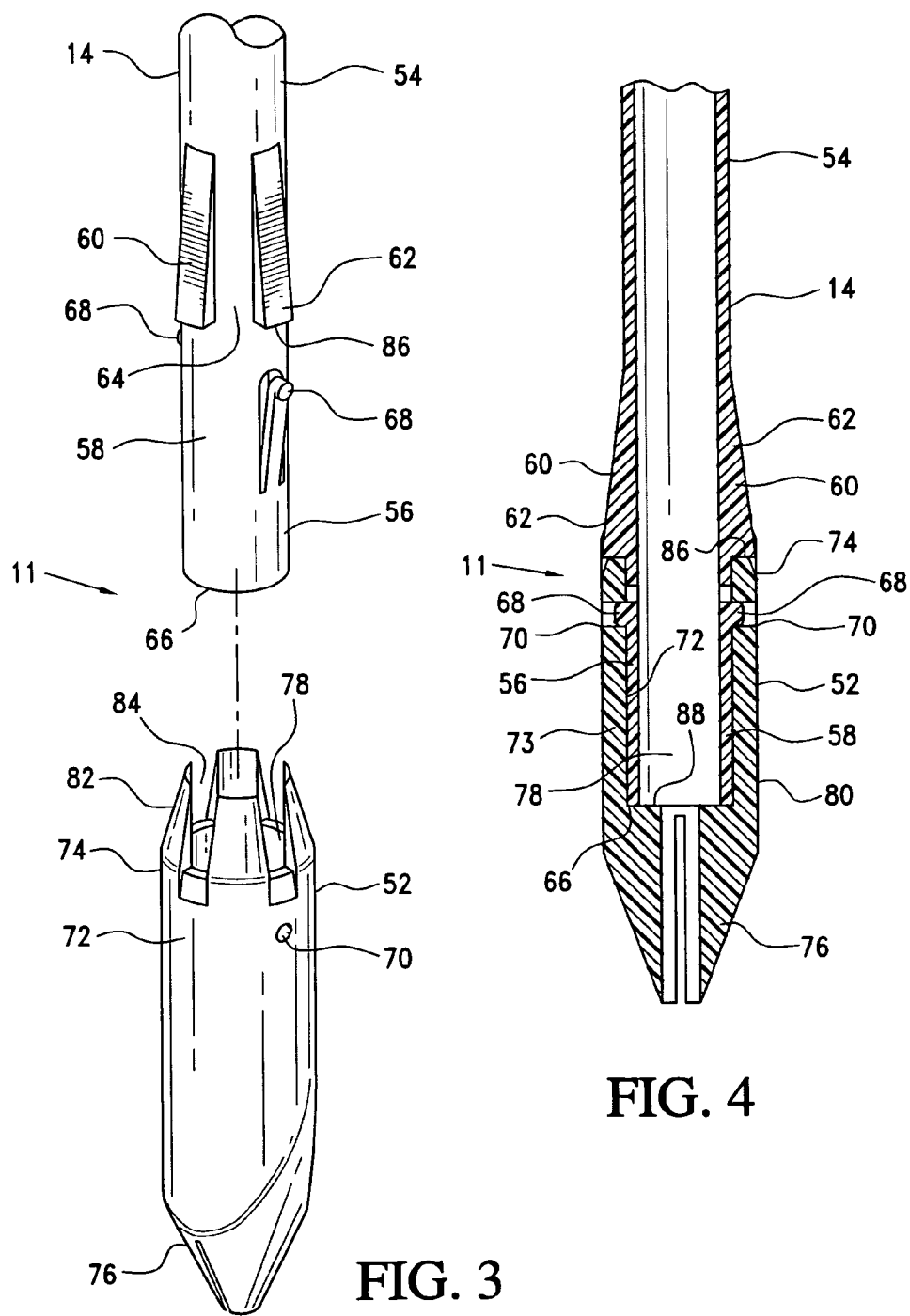
FIG. 3 is a detailed exploded view of the trocar obturator tip.
FIG. 4 is a cross sectional view along the line 4-4 in FIG. 2.
Figure 5:
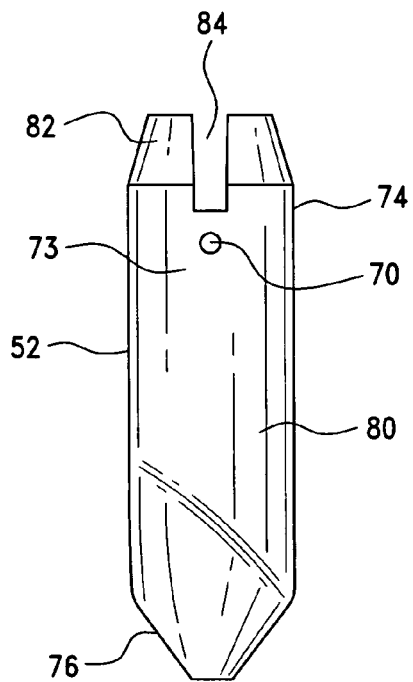
FIGS. 5, 6, 7 and 8 are various views of the tip disclosed in accordance with the present invention.
Figure 7:
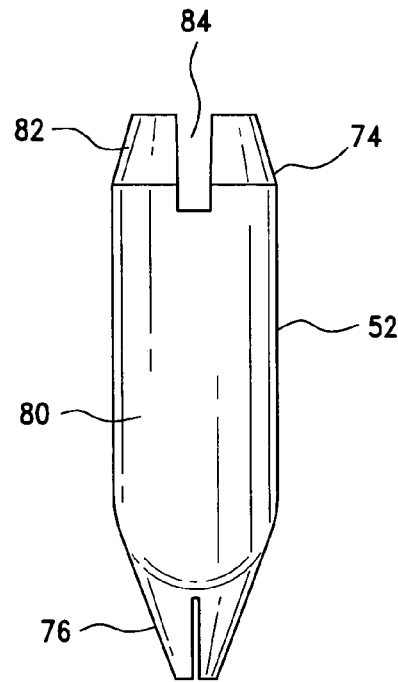
Figure 6:
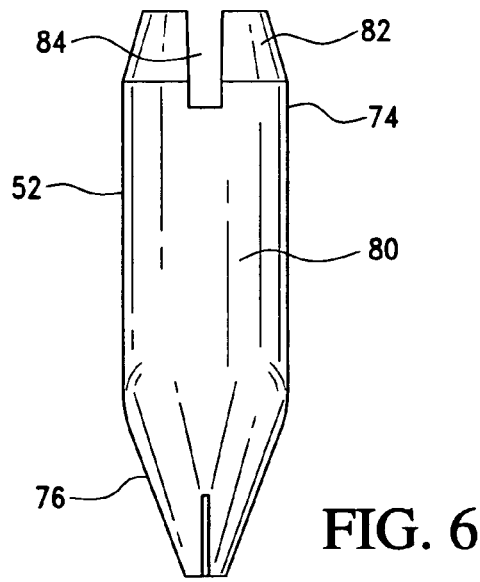
Figure 8:
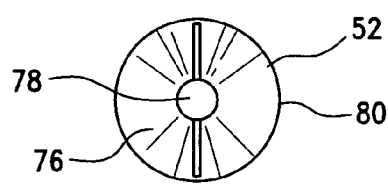

Referring to FIGS. 3 and 4, the distal end 56 of the shaft 54 includes a landing area 58 upon which the tip member 52 is mounted. The landing area 58 is formed with a series of circumferentially oriented abutment members 60. The raised abutment members 60 define alternating raised and lowered sections 62, 64 along the circumference at the distal end 56 of the shaft 54.

As will be appreciated based upon the following disclosure, the abutment members 60 are spaced from the distal tip 66 of the shaft 54 to create and define the landing area 58 upon which the tip member 52 is mounted for assembly of the present trocar obturator 14.

Adjacent the raised and lowered sections 62, 64 defined by the abutment members 60 are first and second resiliently biased snap coupling members 68. In accordance with a preferred embodiment of the present invention, the snap coupling members 68 are positioned between the abutment members 60 and the distal tip 66 of the shaft 54. In this way, the snap coupling members 68 sit within respective recesses 70 formed along the tip member 52 in a position offering ideal strength characteristics. While the position of the snap coupling members is disclosed herein in accordance with a preferred embodiment of the present invention, the snap coupling members may be positioned at other locations along the landing area and different numbers of snap coupling members may be provided without departing from the spirit of the present invention. While a specific coupling structure is disclosed in accordance with a preferred embodiment of the present invention, it may be varied without departing from the spirit of the present invention; for example screw threads, adhesive, a friction or tapered fit, or a coupling pin could be used.

In accordance with a preferred embodiment of the present invention, the snap coupling members 68 are positioned on opposite sides of the landing area 58 for engagement with opposed walls of the tip member 52 upon placement of the tip member 52 over the landing area 58. As will be discussed below in greater detail, the snap coupling members 68 are designed for engagement within recesses 70 formed along the inner wall 73 of the tip member 52. As such, when the tip member 52 is slid over the shaft 54, the snap coupling members 68 bias for coupling with the tip member 52 such that they come into contact with the recesses 70 at which time they expand within the recesses 70 securely coupling the tip member 52 to the shaft 54.

With regard to the tip member 52, it is a substantially elongated member having a first end 74 and a second end 76 with a central aperture 78 extending therethrough. The tip member 52 includes an inner surface 72 and an outer surface 80. The inner surface 72 is formed with a series of recesses 70 shaped and dimensioned for engagement with the snap coupling members 68 of the shaft 54. As such, and as discussed above, when the tip member 52 is slid over the shaft 54, the snap coupling members 68 are at first inwardly biased as the tip member 52 rides thereover. However, when the snap coupling members 68 are aligned with the recesses 70, the snap coupling members 68 extend outwardly into the recesses 70 securely coupling the tip member 52 to the distal end 56 of the shaft 54.

The extended interface between the tip member 52 and the distal end 56 of the shaft 54 is achieved by providing the first end 74 of the tip member 52 with cutout sections shaped and dimensioned to fit within the raised and lowered sections 62, 64 defined by the abutment members 60 at the distal end 56 of the shaft 54. More particular, the first end 74 of the tip member 52 is provided with a series of extension arms 82 shaped and dimensioned to fit between the abutment members 60 within the lowered sections 64 of the landing area 58. In this way, the first end 74 of the tip member 52 fits within the alternating raised and lowered sections 62, 64 at the distal end 56 of the shaft 54 creating an interlocking keyed coupling structure. This allows for a substantial overlap between the tip member 52 and the shaft 54. This also allows for ideal alignment of the tip member 52 and the shaft 54. In addition to providing a coupling structure, the geometry employed in accordance with the present invention provides greater torsional strength characteristics.

Controlled insertion of the shaft 54 within the tip member 52 is facilitated by the interaction between the first end 74 of the tip member 52 and the abutment members 60 of the landing area 58. As the tip member 52 is inserted over the distal end 56 of the shaft 54, the recessed sections 84 between the extension arms 82 of the tip member 52 come into contact with respective faces 86 of the abutment members 60 to limit the insertion of the tip member 52.

Insertion of the tip member 52 over the distal end 66 of the shaft 54 is further controlled by a reduced diameter section along the inner surface 72 of the tip member 52. The reduced diameter section defines an inwardly directed lip 88 which engages the distal tip 66 of the shaft 54 to control the insertion of the landing area 58 of the shaft 54 within the tip member 52. As such, the distal end 56 of the shaft 54 may only extend so far within the tip member 52 before the lip 88 contacts the distal end 56 of the shaft 54 and the shaft 54 may not be pushed any further. In addition, controlled positioning is achieved by the mating surfaces at the first end 74 of the tip member 52 which engage the raised and lowered sections to limit movement of the tip member 52 relative to the shaft 54.

In addition to providing for improved overlap between the tip member 52 and the shaft 54, the extension arms 82 at the first end 74 of the tip member 52 are tapered downwardly as they extend away from the second end 76 of the tip member 52. In fact, the extension arms 82 taper down to a diameter substantially equivalent to that of the outer surface of the shaft member 54. The raised portions 62 of the shaft member 54 are similarly tapered upwardly such that they substantially correspond to the diameter along the outer surface of the tip member 54 at the point where the faces 86 of the abutment members 60 are adjacent to the recessed sections 84 of the first end 74 of the tip member 52. In this way, a nicely tapered surface is achieved at the keyed engagement joint formed between the tip member 52 and the shaft 54. This also provides for added resistance and strength against torsional loads.

Because the first end 74 of the tip member 52 extends different lengths (that is, the first end 74 of the tip member 52 is provided with a series of extension arms 82) to fit within the raised and lowered sections 62, 64 of the shaft member 54, pressure created by the interaction between seal members and the tip member 52 is substantially reduced. In particular, the seal member is not simultaneously confronted with the joint between the tip member 52 and the shaft 54, but rather is sequentially confronted with the various engagement joints formed along the interlocking joint between the tip member 52 and the shaft 54. It is contemplated there could be different numbers of raised and lowered sections without departing from the spirit of the present invention. For example, it could be as few as three sections or as many as ten to twelve sections. It is further contemplated that a sinusoidal joint could be employed within the spirit of the present invention.

This construction of the present trocar obturator tip eliminates the possibility of the seal member falling into the groove at the interlocking joint and retarding penetration or extraction. More particular, the mating surfaces of the shaft 54 and the tip member 52 prevent the seal from lodging between the shaft 54 and the tip member 52. This construction provides the seal with as little a gap as possible to fit into. Because of tolerancing, a line-to-line fit is not practical.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A trocar obturator, comprising:
 a shaft having a proximal end and a distal end including a landing area, the shaft also including an outer surface;
 a tip member secured to the distal end of the shaft, the tip member including a first end and a second end, as well as an outer surface wherein the first end of the tip member is shaped and dimensioned to fit over the landing area of the shaft;
 wherein a coupling structure links the tip member to the shaft, and the shaft adjacent the tip member tapers to a surface diameter substantially coextensive with the outer surface of the tip member, and the tip member adjacent the shaft tapers to a surface diameter substantially coextensive with the outer surface of the shafts;

wherein the landing area includes a plurality of abutment members circumferentially oriented about the shaft defining raised sections and lowered sections along the distal end of the shaft, and the first end of the tip member includes extension arms shaped and dimensioned to fit between the abutment members creating an interlocking keyed coupling structure wherein the first end of the tip member extends different lengths to fit within the raised and lowered sections along the distal end of the shaft and the abutment members contact the first end of the tip member in recessed sections between the extension arms to define a series of spaced engagement joints between distal faces of the respective abutment members and the recessed sections at the first end of the tip member, the extension arms are tapered downwardly as they extend away from the second end of the tip member and the raised portions of the shaft taper upwardly as they extend toward the distal end of the shaft.

2. The trocar obturator according to claim 1, wherein the abutment members are substantially coextensive with the portion of the tip member adjacent the shaft.

3. The trocar obturator according to claim 2, wherein the extension arms are substantially coextensive with the portion of the shaft adjacent the tip member.

4. The trocar obturator according to claim 1, wherein the shaft includes a coupling member along the distal end thereof for engagement with the tip member.

5. The trocar obturator according to claim 4, wherein the coupling member is a snap coupling member biased to seat within a recess formed along an inner surface of the tip member.

6. The trocar obturator according to claim 5, wherein the shaft includes a plurality of snap coupling members biased to seat within respective recesses formed along the inner surface of the tip member.

7. The trocar obturator according to claim 1, wherein the tip member includes an inner surface in which the distal end of the shaft is mounted during assembly, and the inner surface includes an inwardly directed lip limiting movement of the tip member relative to the shaft.

8. The trocar obturator according to claim 1, wherein the tip member includes an inner surface in which the distal end of the shaft is mounted during assembly, and the inner surface includes an inwardly directed lip limiting movement of the tip member relative to the shaft.

9. The trocar obturator according to claim 1, wherein the coupling structure is a keyed coupling structure.

10. A trocar assembly, comprising:
a trocar cannula including a proximal end and distal end; and
a trocar housing coupled to the proximal end of the trocar cannula for receiving and guiding a trocar obturator through the trocar cannula;
the trocar obturator includes a shaft having a proximal end and a distal end including a landing area, the shaft also including an outer surface; the trocar obturator also includes a tip member secured to the distal end of the shaft, the tip member including a first end and a second end, as well as an outer surface wherein the first end of the tip member is shaped and dimensioned to fit over the landing area of the shaft; and wherein a coupling structure links the tip member to the shaft, and the shaft adjacent the tip member tapers to a surface diameter substantially coextensive with the outer surface of the tip member, and the tip member adjacent the shaft tapers to a surface diameter substantially coextensive with the outer surface of the shaft; wherein the landing area includes a plurality of abutment members circumferentially oriented about the shaft defining raised sections and lowered sections along the distal end of the shaft, and the first end of the tip member includes extension arms shaped and dimensioned to fit between the abutment members creating an interlocking keyed coupling structure wherein the first end of the tip member extends different lengths to fit within the raised and lowered sections along the distal end of the shaft and the abutment members contact the first end of the tip member in recessed sections between the extension arms to define a series of spaced engagement joints between distal faces of the respective abutment members and the recessed sections at the first end of the tip member, the extension arms are tapered downwardly as they extend away from the second end of the tip member and the raised portions of the shaft taper upwardly as they extend toward the distal end of the shaft.

11. The trocar assembly according to claim 10, wherein the abutment members are substantially coextensive with the portion of the tip member adjacent the shaft.

12. The trocar assembly according to claim 11, wherein the extension arms are substantially coextensive with the portion of the shaft adjacent the tip member.

13. The trocar assembly according to claim 10, wherein the shaft includes a coupling member along the distal end thereof for engagement with the tip member.

14. The trocar assembly according to claim 13, wherein the coupling member is a snap coupling member biased to seat within a recess formed along an inner surface of the tip member.

15. The trocar assembly according to claim 14, wherein the shaft includes a plurality of snap coupling members biased to seat within respective recesses formed along the inner surface of the tip member.

16. The trocar assembly according to claim 10, wherein the tip member includes an inner surface in which the distal end of the shaft is mounted during assembly, and the inner surface includes an inwardly directed lip limiting movement of the tip member relative to the shaft.

17. The trocar assembly according to claim 10, wherein the tip member includes an inner surface in which the distal end of the shaft is mounted during assembly, and the inner surface includes an inwardly directed lip limiting movement of the tip member relative to the shaft.

18. The trocar assembly according to claim 10, wherein the coupling structure is a keyed coupling structure.

* * * * *